United States Patent
Krieg et al.

(10) Patent No.: US 10,533,943 B2
(45) Date of Patent: Jan. 14, 2020

(54) METHOD AND APPARATUS FOR IDENTIFYING PLASTICS AND/OR THE ADDITIVES THEREIN

(71) Applicant: Unisensor Sensorsysteme GmbH, Karlsruhe (DE)

(72) Inventors: Gunther Krieg, Karlsruhe (DE); Dirk Fey, Neewiller (FR); Juergen Bohleber, Bühl (DE); Heinz Langhals, Ottobrunn (DE); Thorben Schluecker, Ottobrunn (DE); Dominik Zgela, München (DE)

(73) Assignee: UNISENSOR SENSORSYSTEME GMBH, Karlsruhe (DE)

( * ) Notice: Subject to any disclaimer, the term of this patent is extended or adjusted under 35 U.S.C. 154(b) by 0 days.

(21) Appl. No.: 15/548,874

(22) PCT Filed: Feb. 5, 2016

(86) PCT No.: PCT/DE2016/200076
§ 371 (c)(1),
(2) Date: Aug. 4, 2017

(87) PCT Pub. No.: WO2016/124197
PCT Pub. Date: Aug. 11, 2016

(65) Prior Publication Data
US 2018/0038793 A1 Feb. 8, 2018

(30) Foreign Application Priority Data

Feb. 6, 2015 (DE) .......... 10 2015 001 522
Feb. 6, 2015 (DE) .......... 10 2015 001 523
(Continued)

(51) Int. Cl.
*B07C 5/342* (2006.01)
*G01N 21/64* (2006.01)
(Continued)

(52) U.S. Cl.
CPC .......... *G01N 21/6408* (2013.01); *B07C 5/342* (2013.01); *B07C 5/3412* (2013.01);
(Continued)

(58) Field of Classification Search
CPC ..... B07C 5/342; B07C 5/3425; B07C 5/3427; B07C 2501/0054; G01N 21/6408;
(Continued)

(56) References Cited

U.S. PATENT DOCUMENTS 5,201,921 A * 4/1993 Luttermann .......... B07C 5/3427
209/3.3
5,317,162 A * 5/1994 Pinsky ............... G01N 15/1459
250/459.1
(Continued)

FOREIGN PATENT DOCUMENTS

DE 42 31 477 3/1994
DE 44 33 937 3/1996
(Continued)

OTHER PUBLICATIONS

PCT, International Search Report and Written Opinion, International Application No. PCT/DE2016/200076; dated Aug. 17, 2017, 19 pages.
(Continued)

*Primary Examiner* — Joseph C Rodriguez
(74) *Attorney, Agent, or Firm* — Seed Intellectual Property Law Group LLP (57) ABSTRACT

The invention provides a method for identifying plastics and/or the additives therein, wherein at least some of the plastic material is irradiated with light of at least one wavelength, at least some of the light reflected by the plastic material is detected and analyzed, and the plastic material and/or the additive therein is/are identified on the basis of the result of the analysis. The disclosed method utilizes a
(Continued)

fluorescence decay time constant of the intrinsic fluorescence of the plastic material and, if applicable, of the additive(s) therein, which is determined on the basis of the detected light, and the plastic material and/or the additive(s) therein is/are identified on the basis of the determined fluorescence decay time constant.

26 Claims, 5 Drawing Sheets

(30) Foreign Application Priority Data

Feb. 6, 2015 (DE) .................. 10 2015 001 524
Feb. 6, 2015 (DE) .................. 10 2015 001 525

(51) Int. Cl.
*B29B 17/02* (2006.01)
*G01J 3/44* (2006.01)
*G01J 3/18* (2006.01)
*B07C 5/34* (2006.01)

(52) U.S. Cl.
CPC ............ *B07C 5/3427* (2013.01); *B29B 17/02* (2013.01); *G01J 3/18* (2013.01); *G01J 3/4406* (2013.01); *G01N 21/643* (2013.01); *B07C 2501/0054* (2013.01); *B29B 2017/0203* (2013.01); *B29B 2017/0279* (2013.01); *B29K 2995/0035* (2013.01); *G01N 2021/6417* (2013.01); *G01N 2201/06113* (2013.01); *Y02W 30/622* (2015.05)

(58) Field of Classification Search
CPC .......... G01N 21/6413; G01N 21/6415; G01N 21/6417; G01N 21/6419; G01N 21/6421; B29B 2017/0203; B29B 2017/0213; B29B 2017/0279
See application file for complete search history.

(56) References Cited

U.S. PATENT DOCUMENTS

| | | | |
|---|---|---|---|
| 5,329,127 A | 7/1994 | Becker et al. | |
| 5,555,984 A * | 9/1996 | Sommer, Jr. | .......... B07C 5/3416 209/580 |
| 5,909,278 A * | 6/1999 | Deka | .................. G01J 3/4406 250/461.1 |
| 6,049,380 A * | 4/2000 | Goodwin | ........... G01N 21/6428 250/458.1 |
| 6,741,346 B1 * | 5/2004 | Gerstner | ............ G01N 21/6408 250/459.1 |
| RE41,616 E * | 8/2010 | Hubbard | ............ G01N 21/6428 428/412 |
| 2005/0095715 A1 | 5/2005 | Hubbard | |
| 2011/0232398 A1 | 9/2011 | Lambert et al. | |
| 2012/0329944 A1 | 12/2012 | Briffaud et al. | |
| 2014/0363840 A1* | 12/2014 | Mycek | ............... G01N 33/5005 435/29 |

FOREIGN PATENT DOCUMENTS

| | | |
|---|---|---|
| DE | 102012012772 | 12/2013 |
| EP | 0 563 998 | 10/1993 |
| EP | 1 052 499 A1 | 11/2000 |
| GB | 2 330 409 A | 4/1999 |
| TW | I 468653 | 1/2015 |

OTHER PUBLICATIONS

Anonymous: "Fluoreszenzlebensdauer—Wikipedia," (Jul. 24, 2012), XP055288692, Gefunden im Internet: URL:http://web.archive.org/web/20120724053431/http://de.wikipedia.org/wiki/Fluoreszenzlebensdauer, 2 pages.

Heinz Langhals et al: "High Performance Recycling of Polymers by Means of Their Fluorescence Lifetimes*" Green and Sustainable Chemistry, Bd. 04, Nr. 03, (Aug. 2014), XP055287985, ISSN: 2160-6951, DOI: 10.4236/gsc.2014.43019, 8 pages.

Ltd Edinburgh Instruments: "Operating Instructions F900 Fluorescence Spectrometer Software," 2004, Issue 1, XP055288367, Gefunden im Internet: URL:https://www.tcd.ie/Physics/research/groups/ld-nanostructures/resources/equipment/NIRPL.pdf, 116 pages.

* cited by examiner

METHOD AND APPARATUS FOR IDENTIFYING PLASTICS AND/OR THE ADDITIVES THEREIN

German patent applications DE 10 2015 001 525.7, DE 10 2015 001 524.9, DE 10 2015 001 522.2 and also DE 10 2005 001 523.0 are hereby incorporated by reference.

The invention relates to a method for identifying plastics and/or their additives, where at least one sample of a plastic and optionally of its one or more additives is irradiated with light of at least one wavelength, at least part of the light re-emitted by the sample is detected and analyzed, and where the plastic and optionally its additive(s) are identified from the result of the analysis.

The invention further relates to an apparatus for implementing a method for identifying plastics and/or at least one of their additives, the apparatus comprising a light source for irradiating at least one sample of a plastic with light of at least one wavelength, a detector for detecting at least part of the light re-emitted by the sample, an analytical unit comprising at least one processor for analyzing the detected light, and an identification unit for identifying the plastic and optionally its additive or additives from the result of the analysis provided by the analytical unit.

Although it may be applied to any desired fields, the present invention is elucidated in relation to recycling of plastics.

Plastics recycling has experienced increasing significance in recent times. Plastics waste is already of considerable consequence for the environment, whether through the pollution of bodies of water or the ever-increasing volume of plastics waste. One solution to the problem is offered by plastics recycling, in which used plastics, these being plastics which have been processed into products and are no longer needed, are converted into materials of value, in other words materials which are suitable for renewed processing into products. By this means it is then also possible to conserve the resources required for the production of plastics.

In the case of plastics in the form of thermoplastics, for example, re-use is possible via simple melting and reshaping; however, these plastics cannot be readily mixed with other plastics. Furthermore, the identification of plastics is vital for their recycling. Where plastics are similar chemically, as in the case, for example, of polyethylene PE, low-density polyethylene LDPE, high-density polyethylene HDPE, or the like, this is costly and difficult.

Other plastics, such as silicones, for example, have to date not been recycled to any great degree. The reason for this is not only that the incidence of used silicone is substantially smaller in relation to other plastics, but also that it is not possible to separate mixed silicones in respect of the diverse varieties of silicone. Since, however, silicones in some cases have valuable auxiliaries added to them, such as platinum catalysts, for example, there is a great interest both economically and technologically in the targeted recovery of such auxiliaries.

Plastics are also used in the area of food and drink, as for example in the form of PET bottles, whose advantages over glass are many—for example, weight saving, high stability, proof against fracture, and transparency. The re-use or recycling of such bottles for food-and-drink purposes, however, requires the reliable removal of problematic material by sorting, as for example of bottles in which mineral oils have been stored. Lipophilic substances of this kind are partially dissolved in the lipophilic plastics material of the bottle, and so represent a serious contamination (or, generally, an additive) in relation to re-use of the corresponding bottle for foods and drinks, since in certain circumstances the substances partially dissolved in the plastic diffuse out of the plastics material again and may pass into the food or drink contained in the bottle.

In addition to the aforementioned platinum catalysts in the area of the silicones, a variety of additives are also admixed to many plastics. For example, certain flame retardants are admixed to plastics in order to prevent ignition. They are employed in fields including those of electronic devices or of automobiles, in order to prevent ignition or at least to slow it down or to inhibit it. Because of their partial persistence and tendency toward bioaccumulation, the retardants are more and more being replaced by different, less problematic flame retardants; ultimately, however, the retardants are still contained within used equipment and must therefore be considered at least in the context of recycling.

A variety of optical methods have been disclosed for the detection and identification of plastics, in—for example—DE 10 2012 012 772.3 or US 2005/0095715.

A problem in this context, however, is that these methods lack sufficient accuracy, particularly in respect of chemically similar plastics. Another problem is that they require markers for the identification of the plastic, something which, however, is impracticable or extremely costly and inconvenient.

It is an object of the invention, therefore, to specify a method and an apparatus for quick and reliable identification of plastics and/or their additives. A further object of the present invention is to reliably distinguish plastics, especially chemically similar plastics. Furthermore, it is an object of the present invention to specify a method and an apparatus which are simple to implement or realize. Another object of the present invention is to specify an alternative method and alternative apparatus for identifying plastics and/or their additives.

The present invention achieves the above objects, in the case of a method for identifying plastics and/or at least one of the additives thereof, where at least one sample of a plastic is irradiated with light of at least one wavelength, at least part of the light re-emitted by the sample is detected and analyzed, and where the plastic and/or at least one of the additives are identified from the result of the analysis, by the fact that a fluorescence decay time constant of the intrinsic fluorescence of the plastic and/or optionally of at least one of the additives is determined from the light detected, and the plastic and/or optionally at least one of the additives are identified from the fluorescence decay time constant determined.

The present invention achieves the above objects likewise, in the case of an apparatus for identifying plastics and/or at least one of their additives, suitable for implementing a method for identifying plastics and/or at least one of their additives, the apparatus comprising: a light source for irradiating at least one sample of the plastic with light of at least one wavelength, a detector for detecting at least part of the light re-emitted by the sample, an analytical unit comprising at least one processor for analyzing the detected light, and an identification unit for identifying the plastic and/or at least one of its additives from the result of the analysis provided by the analytical unit, by the fact that the analytical unit is designed to determine a fluorescence decay time constant of the intrinsic fluorescence of the plastic from the light detected, and the identification unit is designed to identify the plastic and/or at least one of its additives from the fluorescence decay time constant determined.

Furthermore, the apparatus achieves the above objects by the use of the determination of the singly and/or multiply exponential fluorescence decay time constant for identifying plastic and/or its one or more additives.

One of the advantages achieved therewith is that using the fluorescence decay time of the intrinsic fluorescence allows detection to be very highly reliable. Another advantage is that ease of implementation is enabled in conjunction with reliable evaluation and hence also reliable identification. A further advantage is that even chemically similar plastics can be reliably distinguished and identified. An advantage, furthermore, is that non-plastics, such as rubber, wood or the like, can also be identified and then, where appropriate, also removed. Another advantage is that, in particular, flame retardants which are admixed to plastics can be reliably identified.

In other words, the apparatus and the method allow identification of plastics and, if present, of additives in the plastic as well. It is therefore likewise possible also to ascertain only the additive or only the type of plastic. It is therefore likewise possible also to determine not only plastic but also one or more additives.

The term "plastic", especially in the claims, preferably in the description, refers to any kind of polymer or polymers, examples being     any kind of silicone or silicone polymer, more particularly silicone Tectosil pellet, silicone Tectosil film, silicone Dehesive Sn, silicone Dehesive Pt, any kind of silicone tubes, etc.,     any kind of polyethylene PE, such as LDPE, HDPE, and UHDPE, for example,     polymethyl methacrylate PMMA,     polystyrene PS,     polycarbonate PC,     polyethylene terephthalate PET.

The term "additive", especially in the claims, preferably in the description, refers to any wanted or unwanted additions to plastics, more particularly flame retardants, preferably halogenated, more particularly brominated and/or chlorinated flame retardants, comprising for example     polybrominated diphenyl ether PDBE,     polybrominated biphenyl PBB,     decabrominated diphenyl ether,     pentabrominated diphenyl ether,     octabrominated diphenyl ether,     hexabromocyclododecane,     tetrabromobisphenol A TBBP-A,     tetrabromophthalic anhydride,     brominated polystyrenes,     brominated phenols,     reactive flame retardants,     antimony trioxide,     antimony pentoxide,     ammonium sulfate,     etc.

The term "measured signal", especially in the claims, preferably in the description, refers to a variable detected, for example, by means of a sensor and provided by the sensor, possibly in a different form, for further transmission or further processing. The term "measured signal" refers not only to the unaltered signal ("raw signal") obtained directly from the sensor but also to an altered, further-processed and/or processed signal.

The term "sample", especially in the claims, preferably in the description, refers in particular to the entirety of the material under investigation, presently the plastic, in the form for example of bottles, flakes, etc., and optionally with additives present.

The term "fluorescence decay time", especially in the claims, preferably in the description, also comprehends the term "fluorescence lifetime", "fluorescence lifetime constant", fluorescence decay time constant", or the like.

The terms "mono", "bi", "tri", and so on, in relation to an exponential function, especially in the claims, preferably in the description, refer in general to a summation of different exponential functions with different parameters, with the terms "mono", "bi", "tri", and so on, referring to the respective number of different exponential functions.

The term "mono-exponential", especially in the claims, preferably in the description, refers in general, for example, to a function f of the form $$f = a_0 + a_1 \exp(t^*x + b) \text{ where } a_0, a_1, x, t, b \in R.$$

The terms "multiply exponential", "multiexponential" or "more highly exponential", especially in the claims, preferably in the description, refer to "bi-exponential", and/or "tri-exponential", etc.

The term "bi-exponential", especially in the claims, preferably in the description, refers in general, for example, to a function f of the form $$f = a_0 + a_1 \exp(t_1^*x + b_1) a_2 \exp(t_2^*x + b_2)$$

where $a_0, a_1, x, t_1, b_1, t_2, b_2, a_2 \in R$.

The term "tri-exponential", especially in the claims, preferably in the description, refers in general, for example, to a function f of the form $$f = a_0 + a_1 \exp(t_1^*x + b_1) + a_2 \exp(t_2^*x + b_2) + a_3 \exp(t_3^*x + b_3)$$

where $a_0, a_1, x, t_1, b_1, t_2, b_2, a_2, t_3, b_3, a_3 \in R$.

Further preferred embodiments, advantages, and features of the invention are evident from or disclosed by the following text:

Advantageously, the multiply exponential fluorescence decay time constants are determined and multiexponentially analyzed. By taking account, for example, of bi-exponential or tri-exponential fluorescence decay time constants, it is possible to detect the plastic and/or its additive or additives more easily and more reliably. Furthermore, for example, specific charges, as in the case of silicone Dehesives, for example, or else specific processing forms can even be identified reliably. In the case of PET drinks bottles, for example, the plastic and also additive(s) thereof that is or are contaminated with oils or other lipophilic substances, such as gasoline, diesel, and lubricating oils as additives, for example, can be likewise reliably identified by means of bi-, tri- and more highly exponential fluorescence decay time constants. The same also applies to silicones and additive(s) thereof.

Conveniently the plastic is provided with a marking to identify it, which is irradiated by means of the light. This allows even more reliable identification of plastics and/or their additives.

Advantageously the light of at least one wavelength is provided by means of at least one light pulse. Light pulses permit reliably excitation and at the same time subsequent detection of the re-emitted light.

Advantageously the light pulses are generated by means of a semiconductor light source, more particularly in the form of a laser diode or of a light-emitting diode, containing gallium nitride. This allows cost-effective and at the same time simple provision of light pulses.

Conveniently the light is generated by means of a laser. In this way, particularly defined excitation with a small spectral breadth for the subsequent measurement of the re-emitted light is possible. Ultimately this enables reliable determination of the fluorescence lifetime constant.

Advantageously the re-emitted light is detected by means of one or more phase-sensitive detectors for the subsequent analysis. In this way, particularly reliable detection of the re-emitted light is possible, especially in the case of a plurality of phase-sensitive detectors operating in parallel. Furthermore, through the use of phase-sensitive detectors, the electronic complexity for the detection units can be fashioned favorably.

Conveniently a measured signal of the detected light is integrated over at least one defined timespan for determining the fluorescence decay time constant, and more particularly is ascertained. Through the use of integral measurements it is possible for the electronic complexity for the detection units to be fashioned further favorably. Moreover, reliable determination of the fluorescence decay time constant is made possible.

The measured signal is advantageously integrated over a plurality of timespans, more particularly of nonoverlapping timespans. This substantially increases the reliability of determination of the fluorescence decay time constant.

Advantageously the measured signal is integrated separately over two nonoverlapping timespans, the integrated signals being brought into relation with one another and the plastic and/or at least one of its additives being identified from this relation. Relation here should be understood in particular in the mathematical sense and may comprise, in particular, the forming of a quotient of the two measured integrated constituents of the fluorescence decay time constant. From the quotient thus obtained, this can be compared, for example, with reference quotients stored correspondingly, and so the plastic and/or its additives can be determined.

The at least one timespan advantageously corresponds to a falling edge of the measured signal. Thus it is possible, in a simple and at the same time reliable way, to specify a region for the determination of the fluorescence decay time constant, namely on the falling edge of the measured signal plotted against the time.

Advantageously the position of at least one timespan is chosen before and/or after a customary half-life of a fluorescence lifetime. As a result, the signal-to-noise ratio can be improved considerably, since the re-emitted light of the plastic sample measured can be utilized more effectively or more efficiently.

At least one timespan is conveniently between 1 ms and 15 s, more particularly between 7.5 s and 12.5 s, preferably 10 s. With a timespan of this kind, in a particularly flexible way, the particular timespan to be measured can be adapted to the required accuracy and/or to the specific measurement scenario.

Advantageously the fluorescence decay time constant of the plastic and/or its additive or additives to be detected is known approximately, and the selected duration of the light pulses is less than the known fluorescence decay time constant, more particularly by a factor of at least 5, preferably by a factor of at least 10. In this way it is possible for the fluorescence decay time constant to be determined with particular reliability from the re-emitted light, since the excitation light pulse substantially does not disrupt the measurement of the re-emitted light.

Conveniently the duration of the light pulses is less than 1 ms, preferably less than 100 ns, more particularly less than 10 ns, preferably between 5 ns and 10 ns. By this means, the duration chosen for the excitation pulse can be considerably smaller than the fluorescence lifetime. Light pulses of this kind can be generated efficiently using semiconductor lasers, for example.

Advantageously the at least one wavelength is in the range between 200 nm and 600 nm, more particularly between 250 nm and 300 nm, between 375 nm and 450 nm, and between 520 nm and 540 nm, preferably between 260 nm and 270 nm, between 400 nm and 410 nm, and also between 530 nm and 535 nm. By means of the at least one wavelength in this range it is possible, for example, to irradiate a sample of the plastic with UV light and/or visible light, thus enabling reliable detection of the re-emitted light not only in relation to determination of the fluorescence decay time constant, but also opening up the possibility of further analysis on the basis of a further method.

Advantageously, when the plastic and/or its additive or additives have been identified, the identified plastics are separated for recycling by means of a sorting device. In this way, separation of plastics with or without additives is made possible in a simple and reliable way.

Advantageously, an optical grating is disposed in a detection beam path of the re-emitted light, and the fluorescence lifetime constant is determined by means of the zero-order light diffracted by the optical grating. Accordingly, in a simple way, it is possible to carry out not only the determination of the fluorescence decay time constant but also further identification methods by means, for example, of higher-order light.

Conveniently the sample is irradiated multiply in succession with light of the at least one wavelength, and the light re-emitted accordingly is measured and analyzed multiply for determining the fluorescence lifetime constant. This further increases the reliability when determining the fluorescence lifetime constant, since different measurements serve as a basis for the analysis.

The at least two timespans are advantageously assigned to temporally different, more particularly consecutive, irradiations of the sample with light. One of the advantages achieved by this is that the requirements asked of the electronic components for the evaluation are reduced still further as a result, since the measurement is carried out during excitations at different times.

Conveniently the detection of the re-emitted light is triggered by the irradiation of the sample with light. In this way, a time-shifted measurement triggered by the excitation light pulse can be performed, allowing measurement to take place within a fluorescence decay process, particularly in the case of periodic excitation.

Advantageously the light source is a pulsed light source, preferably a pulsed laser. Light pulses allow reliable excitation and, at the same time, subsequent detection of the re-emitted light.

Advantageously the detector is of phase-sensitive design. In this way, particularly reliable detection of the re-emitted light is possible, especially in the case of a plurality of phase-sensitive detectors operating in parallel. Through the use of phase-sensitive detectors, moreover, it is possible for the electronic complexity for the detection units to be fashioned favorably.

Conveniently an optical grating is disposed in a detection beam path of the re-emitted light, the detector being disposed in such a way that the zero order of the light diffracted by the optical grating is detectable by means of the detector, and more particularly a spectrometer being disposed, with which the higher orders of the light diffracted by the optical grating are detectable for spectroscopic evaluation. In this way, simply, it is possible not only to determine the fluorescence decay time constant but also, for example, to generate the entire fluorescence spectrum and then, optionally, also detect it for additional evaluation.

Conveniently a sorting device is disposed which is designed to separate identified plastics from other plastics. With such a device, simply and reliably, the separation and partition of plastics with or without additives is made possible.

Other important features and advantages of the invention are evident from the dependent claims, from the drawings, and from associated description of figures with reference to the drawings.

It will be appreciated that the features identified above and those still to be elucidated below can be used not only in the particular combinations specified but also in other combinations, or on their own, without departing from the scope of the present invention.

Preferred implementations and embodiments of the invention are depicted in the drawings and are elucidated in more detail in the description hereinafter, with identical reference symbols relating to the same or similar or functionally identical components or elements.

Figure 1:
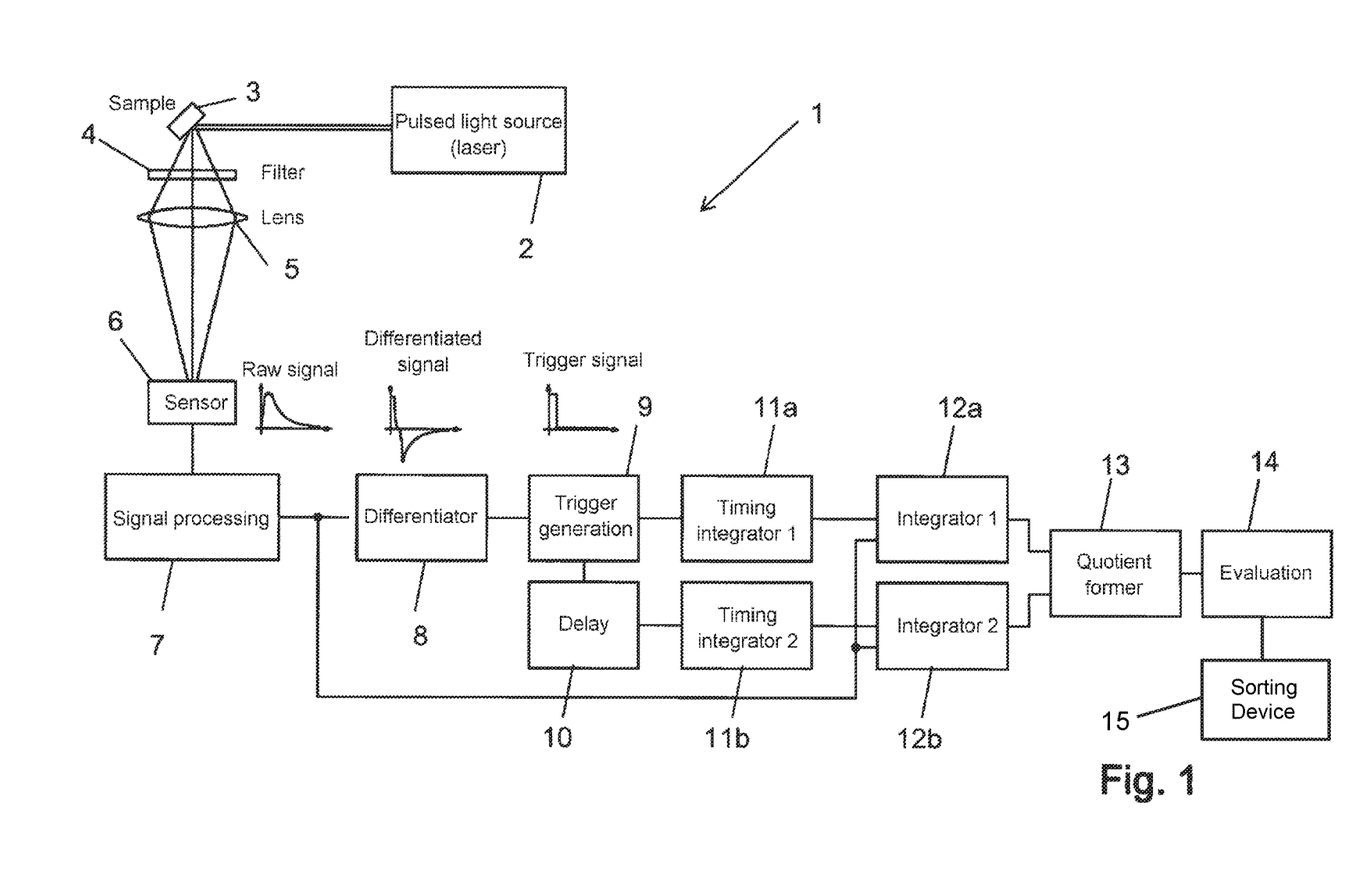
FIG. 1 shows in diagrammatic form an apparatus according to one embodiment of the present invention.

FIG. 1 shows an apparatus for identifying plastic and/or optionally one or more of its additives, 1. This apparatus 1 comprises a pulsed light source 2, here in the form of a laser, which is used to irradiate a sample 3 of the plastic that is to be identified. The light re-emitted by the sample 3 is detected by means of a sensor 6, via a filter 4 and also a lens 5. The raw signal obtained from the sensor 6 is processed by a signal processing element 7, and a differentiated signal is likewise generated by means of a differentiator 8. A trigger is likewise generated, by means of a trigger generation element 9, which then triggers a first timing element integrator 12a and, via a delay 10, a second timing element integrator 12b.

Figure 2:
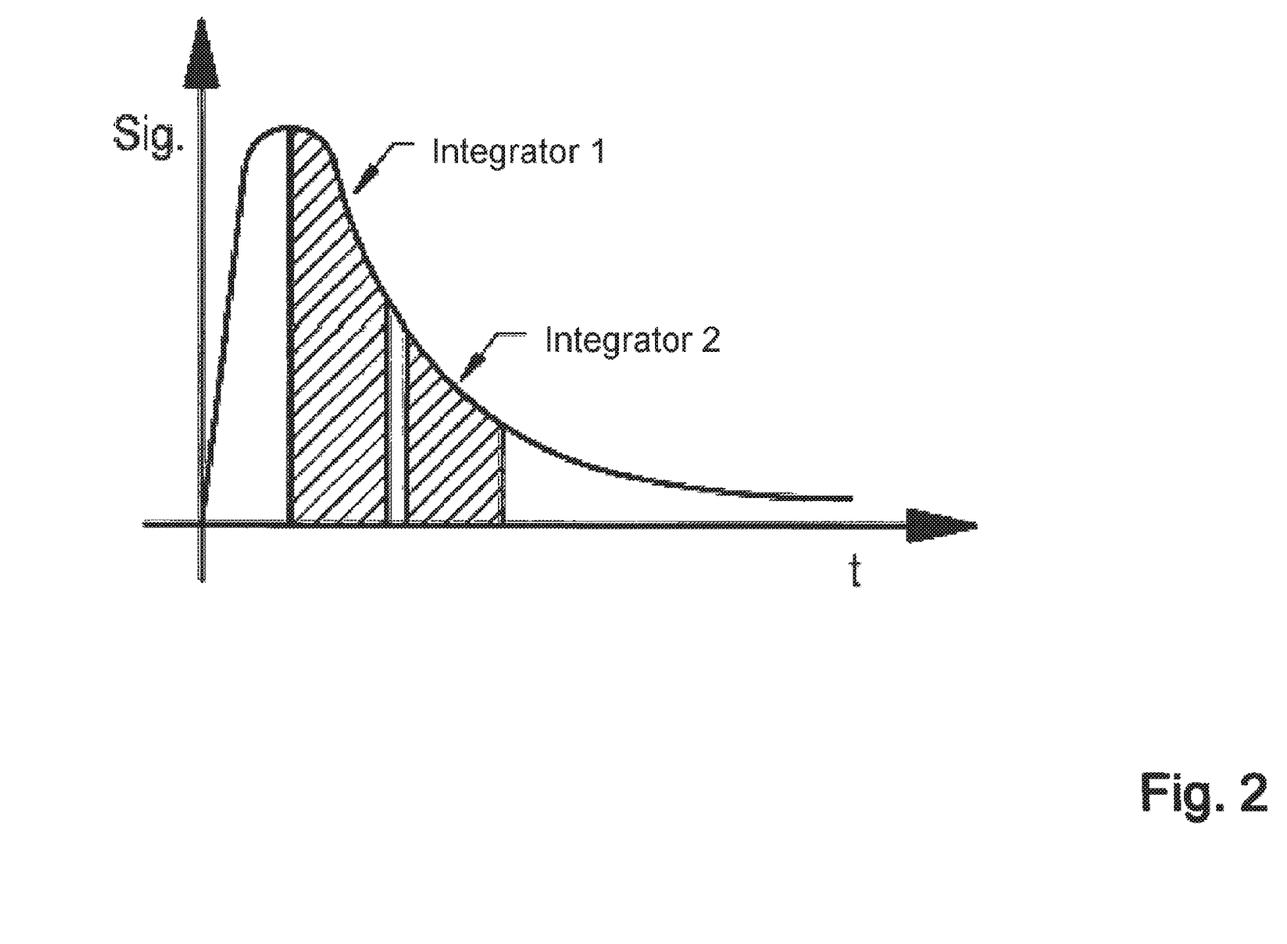
FIG. 2 shows in diagrammatic form parts of a method according to one embodiment of the present invention.

By means of the two integrators 12a and 12b, the signal (see FIG. 2) is integrated at different, nonoverlapping timespans on the falling edge of the processed signal. By means of a quotient former 13, the two values provided by the two integrators 12a and 12b are placed in relation to one another, presently by means of quotient forming, and the number thus obtained is supplied to an evaluation element 14.

The evaluation element 14 may consist, inter alia, of storage in an apparatus memory of a multiplicity of reference parameters for different combinations of plastics and their additives, and of identification of the plastic and/or its additives then on the basis of a comparison between these parameters and the parameter ascertained by the measurement. For the storage of such values/parameters, it is possible, for example, for multiply repeated measurements to be carried out on the same plastic with the same additives, and for these measurements then to be deposited in the memory with an average and a corresponding deviation, for example. In the case of an ambiguous identification, a result of this kind may be displayed accordingly to a user, and the plastic, if the method is being used in the context of recycling, can be removed separately and then, where appropriate, supplied to a further identification process. A sorting device 15 is disposed which is designed to separate identified plastics from other plastics. With such a device, simply and reliably, the separation and partition of plastics with or without additives is made possible.

Figure 3:
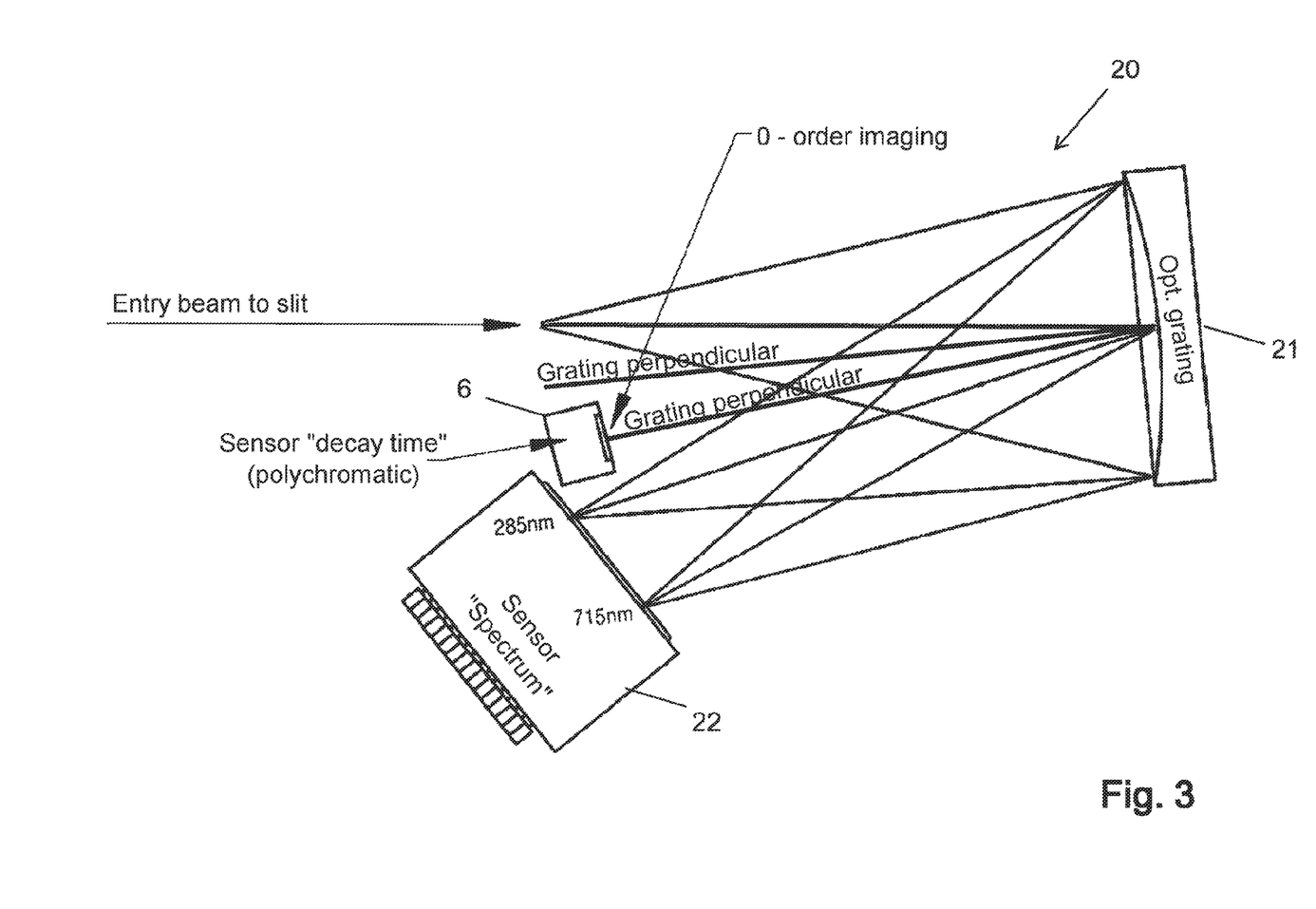
FIG. 3 shows in diagrammatic form parts of an apparatus according to one embodiment of the present invention.

FIG. 3 shows in diagrammatic form parts of an apparatus according to one embodiment of the present invention.

FIG. 3 shows a spectrometer with accessory for measuring the fluorescence decay time. In this case, in the beam path, in particular between lens 5 and sensor in FIG. 1, an optical grating 21 is disposed additionally, and diffracts the light bundled by the lens 5. The sensor 6, which is provided for the re-emitted light for the detection of the fluorescence decay time constant, is in this case disposed in the 0 order of the light diffracted by the optical grating 21. In addition there is a further sensor 22 disposed, which serves for accommodating the higher orders of the diffracted light from the optical grating 21. In this case, this sensor is especially sensitive in the wavelength range between 250 nm and 750 nm, preferably between 285 nm and 715 nm. Accordingly, then, the light re-emitted by the plastic and/or its additives can be analyzed in this spectral range as well.

Figure 4:
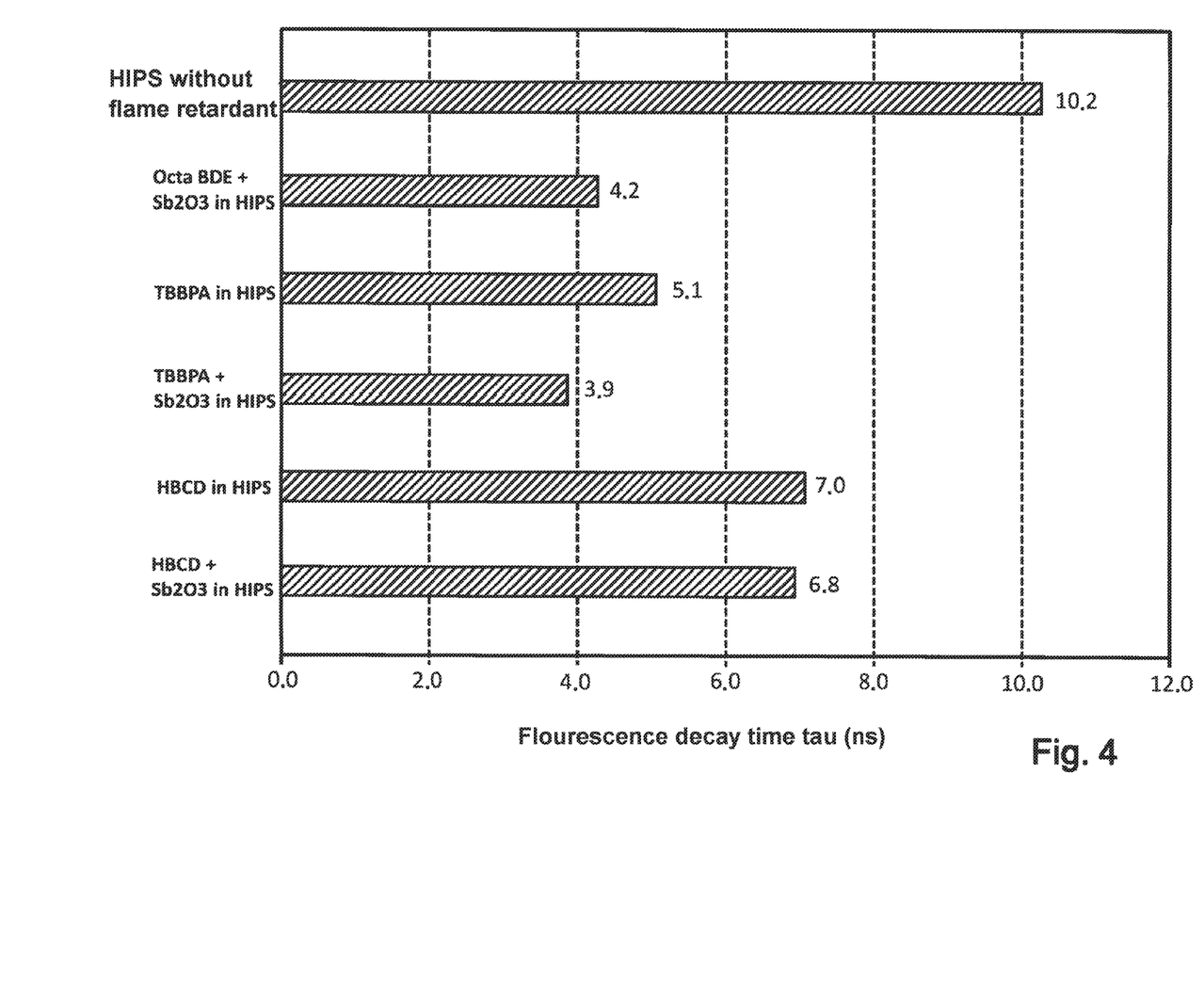
FIG. 4 shows fluorescence decay times in the case of summated fluorescence of polystyrene with and without various flame retardants.

FIG. 4 shows fluorescence decay times with summated fluorescence of polystyrene with and without various flame retardants.

Shown in FIG. 4 are various fluorescence decay times for summated fluorescence with excitation at a wavelength of 266 nm for high-impact polystyrene, HIPS, without flame retardant and with various flame retardants. The wavelength of 266 nm can be generated, for example, using an NdYAG laser, which has a basic wavelength of 1064 nm, by frequency quadrupling in a manner already known. Apparent from FIG. 4 here are significant differences in the fluorescence decay time for different flame retardants. Thus the fluorescence decay time for HIPS without flame retardancy is 10.2 ns, whereas on addition of the flame retardants CBBPA and $Sb_2O_3$ it is lower by more than half, here specifically 3.9 ns.

All in all, it is evident from FIG. 4 that the addition of flame retardants to high-impact polystyrene significantly affects the duration of the fluorescence decay time and is dependent on the flame retardants used. The decay time is lowered in particular by flame retardants present in the plastic, probably due to quench effects.

Figure 5:
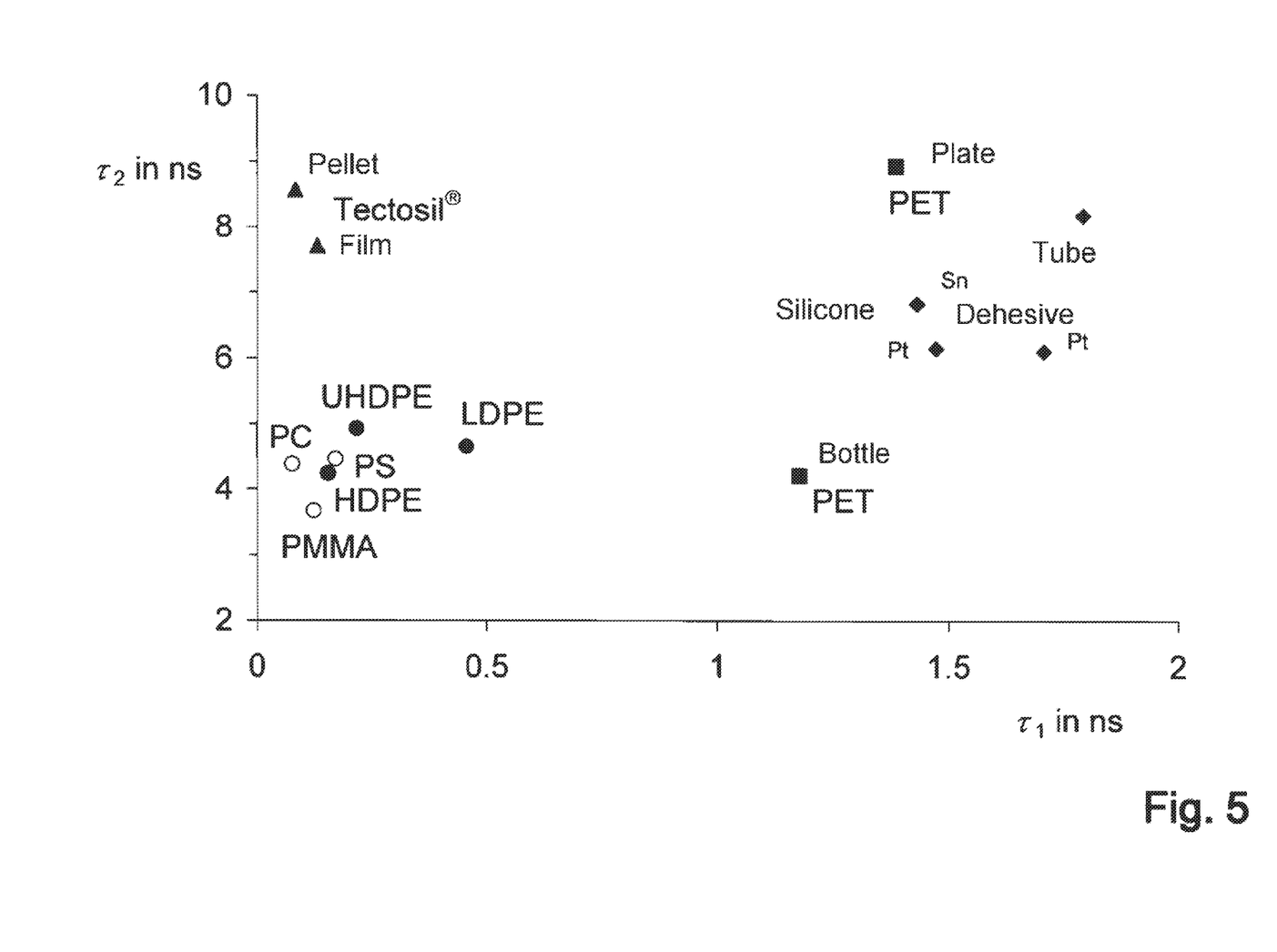
FIG. 5 shows an overview of a bi-exponential evaluation of fluorescence decay times of various materials.

FIG. 5 shows an overview of a bi-exponential evaluation of fluorescence decay times of various materials.

FIG. 5 reproduces the bi-exponential decay times of various plastics materials. In principle, however, even a mono-exponential decay time determination may be sufficient in itself for certain plastics:

| Plastics material | $\tau$ | $\tau_1$ | $\tau_2$ | # |
|---|---|---|---|---|
| Polymethyl methacrylate (PMMA) | 0.841 | 0.124 | 3.669 | 1 |
| Polystyrene (PS) | 3.290 | 0.171 | 4.457 | 2 |

-continued

| Plastics material | τ | $\tau_1$ | $\tau_2$ | # |
|---|---|---|---|---|
| Polycarbonate (PC) | 1.038 | 0.077 | 4.379 | 3 |
| Polyethylene terephthalate (PET) bottle[a] | 1.840 | 1.176 | 4.205 | 4 |
| Polyethylene terephthalate (PET) plate | 4.466 | 1.387 | 8.933 | 5 |
| Polyethylene LDPE | 2.19 | 0.456 | 4.655 | 6 |
| Polyethylene HDPE | <0.2 | 0.155 | 4.238 | 7 |
| Polyethylene UHDPE | 1.58 | 0.217 | 4.932 | 8 |
| Silicone Tectosil ® pellet | | 0.132 | 7.709 | 9 |
| Silicone Tectosil ® film | | 0.084 | 8.572 | 10 |
| Silicone Dehesive Sn | 3.078 | 1.432 | 6.825 | 11 |
| Silicone Dehesive Pt (1) | 3.162 | 1.473 | 6.149 | 12 |
| Silicone Dehesive Pt (2) | 3.114 | 1.707 | 6.106 | 13 |
| Silicone tube | 4.333 | 1.793 | 8.180 | 14 |

[a]PET drinks bottle from a known manufacturer of carbonated beverages.

Shown in the table above are the fluorescence decay constants τ in ns of various technical polymers, averaged over a measuring time of 10 s. Fluorescence excitation took place at a wavelength of 403 nm; mono-exponential evaluation: τ, bi-exponential evaluation: $\tau_1$ and $\tau_2$.

It is apparent from tab. 1 that an assignment can be made in principle simply via the mono-exponential decay time τ (#1 to 8); in the case of silicones, this is already difficult in view of the in some cases very short decay time $\tau_1$ (#9 to 10). Where both decay constants ($\tau_2$ and $\tau_2$) are taken into account, an assignment is substantially easier and more reliable, and it is also possible to carry out assignment not only to the plastic itself, but also, furthermore, to specific charges, as in the case of the silicone Dehesives (#11 to 13), for example, or else to specific processing forms (#4 and 5 and #9 and 10). These relationships are readily apparent from the two-dimensional plotting of $\tau_2$ against $\tau_1$, as shown in FIG. 5; clusters are then found, such as for the various Dehesive films, for example. Via an analysis of this kind, together with the time constant τ of the mono-exponential evaluation, more difficult assignments then become possible too, as in the case of the various grades of polyethylene, for example.

The fluorescence decay times in this case were determined with integration over a time period of 10 s, and resulted in values that were highly reproducible, even for different samples of plastic. The measuring time could easily be shortened even to 1 ms, resulting in measurement values without significantly greater scattering.

For fluorescence excitation, the customary light sources for short light flashes can be and were used—for example, gas discharge lamps (flash lamps), preferably with hydrogen-containing gas fillings, or semiconductor lasers, a wide variety of which are available and whose operation is uncomplicated. The pulse duration can be in the nanosecond range, and the time profile of the fluorescent light as a response to the excitation pulse can be obtained in a known way, by deconvolution, for example. It is not necessary for this purpose, though it is advantageous, if the duration of the excitation pulse is considerably smaller than the fluorescence lifetimes; this can be achieved efficiently using semiconductor lasers.

The fluorescence lifetime spectra were recorded with a PicoQuant FluoTime 300. Serving as the light source was a PicoQuant PicoHarp 300 controlled PC-405 laser with 0.4 mW output at a pulse frequency of 20 MHz and an excitation wavelength of 403 nm.

TABLE 2

Determination of the detection wavelength

| Sample | $t_{Fluo1}$ | $t_{Fluo2}$ | Detection wavelength selected |
|---|---|---|---|
| PMMA | 2-3 ns | 4-100 ns | 440 nm |
| PS | 4-6 ns | 6-100 ns | 490 nm |
| PC | 2-3 ns | 4-100 ns | 440 nm |
| Tectosil pellet | 2-3 ns | 4-100 ns | 480 nm |
| Tectosil film | 2-3 ns | 4-100 ns | 480 nm |
| PET | 2-5 ns | 8-100 ns | 450 nm |
| PE (HDPE) | 2-3 ns | 4-100 ns | 500 nm |

The detection wavelength was determined by recording a lifetime-dependent fluorescence spectrum. In this case, with the corresponding spectral wavelengths, the respective fluorescence intensities of the fluorescence components were recorded with predominantly short fluorescence lifetime ($t_{Fluo1}$) and also with predominantly long fluorescence lifetime ($t_{Fluo2}$). The ranges selected are a consequence of the nature of each sample subjected to measurement, and are not necessarily representative of the individual fluorophores contained in the sample. The detection was performed subsequently at the wavelength corresponding to the fluorescence maximum of the components with long fluorescence lifetime (table 2).

The measurement duration of the fluorescence lifetime determination was 1.0 ms or 10 s. The decay curves thus obtained were evaluated using the FluoFit software from Picoquant. The maximum of the measurement curve was determined for this purpose, and the thereof was considered in respect of two abscissa sections. The first is that between the curve maximum ($t_{max}$) and the corresponding timepoint x ns after the detected maximum intensity ($t_{xns}$) resulting in the fluorescence lifetime $\tau_1$. The second abscissa section, beginning at $t_{yns}$, embraces a range of 40 ns (up to $t_{zns}$), which gives the fluorescence lifetime $\tau_2$ (table 3). The fluorescence lifetimes are obtained by exponential fitting (exponential tail fit) of the respective curve sections in accordance with the formula $I_{rel}=A*e^{-t/\tau}$.

TABLE 3

Selection of time ranges as a function of the decay curve for bi-exponential fitting.

| Sample | $t_{max}$-$t_{xns}$ | $t_{yns}$-$t_{zns}$ |
|---|---|---|
| PMMA | 0-0.5 ns | 3-43 ns |
| PS | 0-0.5 ns | 3-43 ns |
| PC | 0-0.5 ns | 3-43 ns |
| Tectosil pellet | 0-0.5 ns | 2-42 ns |
| Tectosil film | 0-0.5 ns | 2-42 ns |
| PET | 0-3 ns | 5-45 ns |
| PE | 0-3 ns | 3-43 ns |

The excitation structure of the laser was not taken into account here, owing to its low full width at half-maximum. The values obtained are therefore not absolute, but must instead be adapted for specific instruments. In the case of the residual silicones (Dehesive, tube), the deconvoluted data were evaluated bi-exponentially for the purpose of better reproducibility. By this means it is possible to ensure greater reliability in the identification.

Determined below are the fluorescence decay time constants of PET drinks bottles, especially PET water bottles and their shredder material, in order to be able to distinguish it from PET material that has been contaminated with oils and other lipophilic substances such as, for example, autofuel, diesel fuel and lubricating oils (engine oil). This contact may have come about in accordance with function or else by incorrect use—for example, impermissible dispensing of fuels into drinks bottles. The fluorescence decay times found were as follows:

TABLE 4

Fluorescence decay constants τ in ns of PET materials with various contaminants, averaged over a 10 s measuring time. Fluorescence excitation at 403 nm, detection at 450 nm. Mono-exponential evaluation: τ; bi-exponential evaluation: $\tau_1$ and $\tau_2$.

| PET material | τ | $\tau_1$ | $\tau_2$ | # |
|---|---|---|---|---|
| Drinks bottle[a)] | 1.840 | 1.176 | 4.205 | 1 |
| Recyclate flakes[b)] | 1.867 | 0.980 | 5.301 | 2 |
| Bottle, contact with diesel[a,c)] | 0.971 | 0.937 | 3.479 | 3 |
| Bottle, contact with diesel, washed[a,c,d)] | 0.994 | 0.947 | 3.608 | 4 |
| Bottle, contact with engine oil[a,c)] | 1.020 | 0.973 | 4.166 | 5 |
| Bottle, contact with engine oil, washed[a,c,d)] | 1.060 | 1.028 | 3.662 | 6 |
| PET plate | 4.466 | 1.387 | 8.933 | 7 |

[a)]PET drinks bottle from a known manufacturer of carbonated beverages.
[b)]commercial PET recyclate flakes.
[c)]After a week of contact with extraneous substances.
[d)]Washed material; see experimental section.

It can be seen from tab. 4 that for PET of customary drinks bottles, decay constants of a good 1.8 ns are obtained (τ of #1 and 2), which become considerably shorter on contamination with mineral oil products such as diesel oil or engine oil, surprisingly, at 1 ns (#3 and 5). Careful washing does little to change this (#4 and 6). A PET plate (#7) gave considerably higher fluorescence decay times. When account is taken of bi-exponential components ($t_1$ and $t_2$), high values of $\tau_1$ are found analogously for untreated material (#1, 2, and 7), which drop significantly on treatment with mineral oil products (#3 and 5), and no longer attain the original values even after careful washing (#4 and 6); an entirely analogous picture emerges for the $\tau_2$ decay time, and therefore allows an assignment to be made on the basis of two variables. The shortening of the mono-exponential decay constant τ of contaminated material can be ascribed in part to the fact that the longer-lived bi-exponential component, characterized by $\tau_2$, is significantly smaller.

The fluorescence decay times in this case were determined again with integration over a time period of 10 s, and resulted in values that were highly reproducible, even for different samples. The measuring time could easily be shortened to 1 ms, resulting in measurement values without significantly greater scattering.

The detection wavelength was determined here by recording a lifetime-dependent fluorescence spectrum of a PET derivative. In this case, with the corresponding spectral wavelengths, the respective fluorescence intensities of the fluorescence components were recorded with predominantly short fluorescence lifetime ($t_{Fluo1}$=2-5 ns) and also with predominantly long fluorescence lifetime ($t_{Fluo2}$=8-100 ns). The ranges selected are a consequence of the nature of each sample subjected to measurement, and are not necessarily representative of the individual fluorophores contained in the sample. The detection was performed subsequently at the wavelength corresponding to the fluorescence maximum of the components with long fluorescence lifetime (450 nm).

The measurement duration of the fluorescence lifetime determination was 1.0 ms or 10 s. The decay curves thus obtained were evaluated using the FluoFit software from Picoquant. The maximum of the measurement curve was determined for this purpose, and the thereof was considered in respect of two abscissa sections. The first is that between the curve maximum ($t_{max}$) and the corresponding timepoint 3.0 ns after the detected maximum intensity ($t_{3ns}$) resulting in the fluorescence lifetime $\tau_1$. The second abscissa section, beginning at an abscissa section 5 ns after the maximum ($t_{5ns}$), embraces a range of 40 ns (up to $t_{45ns}$), which gives the fluorescence lifetime $\tau_2$. The fluorescence lifetimes are obtained by exponential fitting (exponential tail fit) of the respective curve sections in accordance with the formula $I_{rel}=A*e^{-t/\tau}$.

The excitation structure of the laser was not taken into account here, owing to its low full width at half-maximum. The values obtained are therefore not absolute, but must instead be adapted for specific instruments. The method described, however, illustrates the reliable differentiation of the different samples, and can be adapted to other experimental arrangements.

Cleaning here took place first of all with manual wiping using fabric cloths; in the case of compact PET parts, comminution took place to flakes. Thereafter the PET flakes were washed in a mixture of 3% aqueous NaOH solution (100 mL) and 15% aqueous sodium dodecyl sulfate solution (50 mL) with stirring at 85° C. for 2 h. Lastly, the test specimens were dried with fabric paper and air pressure, and then at 60° C. for 16 h.

In the case of polyethylene, the mono- and bi-exponential fluorescence decay times were likewise determined:

For the LDPE (high-pressure polyethylene), the longest fluorescence decay time of 2.19 ns was found on mono-exponential application, which differs so considerably from the decay time of the other varieties of polyethylene that simple detection is entirely possible. The fluorescence decay times of the low-pressure polyethylene varieties (HDPE and UHDPE) are considerably shorter. Here, however, differentiation is likewise possible, and 1.58 ns is found for UHDPE and, finally, for HDPE the shortest decay time of less than 0.2 ns; for the latter material, a further, supportive method may be desirable on account of the very short decay time. The fluorescence decay curves of the polyethylenes contain high bi-exponential components, and, on bi-exponential evaluation of the curves, 0.456 ns and 4.655 ns are found for LDPE, 0.155 ns and 4.238 ns for HDPE, and 0.217 ns and 4.923 ns for UHPE; see table 5 below. Using the bi-exponential components, the assignment of the polyethylenes is substantially simplified and considerably more reliable.

TABLE 5

Fluorescence decay constants τ in ns of various PE materials, averaged over a 10 s measuring time. Fluorescence excitation at 403 nm, detection at 450 nm. Mono-exponential evaluation: τ, bi-exponential evaluation: $\tau_1$ and $\tau_2$. Stated in parentheses is the standard deviation in the case of a relatively unfavorable 1 ms integration time, for ten independent samples of material.

| PE material | τ | $\tau_1$ | $\tau_2$ | # |
|---|---|---|---|---|
| LDPE | 2.19 | 0.456 (±0.039) | 4.655 (±0.93) | 1 |
| HDPE | <0.2 | 0.155 (±0.013) | 4.238 (±0.77) | 2 |
| UHDPE | 1.58 | 0.217 (±0.022) | 4.923 (±0.91) | 3 |

The values of $\tau_2$ and $\tau_2$ in table 5 were determined with a 10 s integration time and can be considered as reliable average values. To estimate the effect of measurement errors, the standard deviations were determined from the measurements of ten independent samples, with the relatively unfavorable integration time of only 1 ms. Even taking account of the now unfavorable boundary conditions, clear identification of the polymer materials is possible.

The detection wavelength for PE was determined here by recording a lifetime-dependent fluorescence spectrum of a PE derivative (HDPE). In this case, with the corresponding spectral wavelengths, the respective fluorescence intensities of the fluorescence components were recorded with predominantly short fluorescence lifetime ($t_{Fluo1}$=2-3 ns) and also with predominantly long fluorescence lifetime ($t_{Fluo2}$=4-100 ns). The ranges selected are a consequence of the nature of each sample subjected to measurement, and are not necessarily representative of the individual fluorophores contained in the sample. The detection was performed subsequently at the wavelength corresponding to the fluorescence maximum of the components with long fluorescence lifetime (500 nm).

The measurement duration of the fluorescence lifetime determination was again 1.0 ms or 10 s. The decay curves thus obtained were evaluated using the FluoFit software from Picoquant. The maximum of the measurement curve was determined for this purpose, and the thereof was considered in respect of two abscissa sections. The first is that between the curve maximum ($t_{max}$) and the corresponding timepoint 3.0 ns after the detected maximum intensity ($t_{3ns}$) resulting in the fluorescence lifetime $\tau_1$. The second abscissa section embraces, beginning at $t_{3ns}$, a range of 40 ns (up to $t_{43ns}$), which gives the fluorescence lifetime $\tau_2$. The fluorescence lifetimes are obtained by exponential fitting (exponential tail fit) of the respective curve sections in accordance with the formula $I_{rel}=A*e^{-t/\tau}$.

The excitation structure of the laser was again not taken into account here, owing to its low full width at half-maximum. The values obtained are therefore not absolute, but must instead be adapted for specific instruments. The method described, however, illustrates the reliable differentiation of the different samples, and can be adapted to other experimental arrangements.

Furthermore, the mono- and bi-exponential fluorescence decay times were also determined for various silicone materials.

TABLE 6

Fluorescence decay constants τ in ns of various silicone materials, averaged over a 10 s measuring time. Fluorescence excitation at 403 nm, detection at 450 nm. Bi-exponential evaluation: $\tau_1$ and $\tau_2$.

| Silicone material | τ | $\tau_1$ | $\tau_2$ | # |
|---|---|---|---|---|
| Tectosil ® pellet |  | 0.132 | 7.709 | 1 |
| Tectosil ® film |  | 0.084 | 8.572 | 2 |
| Silicone Dehesive Sn | 3.078 | 1.432 | 6.825 | 3 |
| Silicone Dehesive Pt (1) | 3.162 | 1.473 | 6.149 | 4 |
| Silicone Dehesive Pt (2) | 3.114 | 1.707 | 6.106 | 5 |
| Silicone tube | 4.333 | 1.793 | 8.180 | 6 |

It is evident from tab. 6 that the silicones can be assigned unambiguously by way of the two decay constants ($\tau_1$ and $\tau_2$). Two clusters are obtained, with short decay constants $\tau_1$ obtained for the commercial silicone elastomer Tectosil® (#1 and 2), and longer constants for Dehesive materials (#3 to 5). The processing of Tectosil® has a smaller yet characteristic influence (#1 and 2). In comparison to other polymers, the decay constants $\tau_2$ are very long and can be employed for the assignment to silicones and also for the precision assignment. This variable also allows the production of the Dehesive materials to be differentiated, by finding a longer constant on application of a tin catalyst (#3) and a shorter constant in the case of platinum catalysts (#4 and 5). A commercially available silicone tube (#6) tends to correspond in terms of its data to the Dehesive materials, but can be clearly distinguished from them; materials of different manufacturers and for different end uses can therefore be efficiently distinguished and also classified. FIG. 5 shows this in two dimensions.

The fluorescence decay times in this case were determined with integration over a time period of 10 s, and resulted in values that were highly reproducible, even for different samples. The measuring time could easily be shortened to 1 ms, resulting in measurement values without significantly greater scattering.

The fluorescence lifetime spectra were recorded with a PicoQuant FluoTime 300. Serving as the light source was a PicoQuant PicoHarp 300 controlled PC-405 laser with 0.4 mW output at a pulse frequency of 20 MHz and an excitation wavelength of 403 nm.

The detection wavelength was determined by recording a lifetime-dependent fluorescence spectrum of Tectosil (pellet). In this case, with the corresponding spectral wavelengths, the respective fluorescence intensities of the fluorescence components were recorded with predominantly short fluorescence lifetime ($t_{Fluo1}$=2-3 ns) and also with predominantly long fluorescence lifetime ($t_{Fluo2}$=4-100 ns). The ranges selected are a consequence of the nature of each sample subjected to measurement, and are not necessarily representative of the individual fluorophores contained in the sample. The detection was performed subsequently at the wavelength corresponding to the fluorescence maximum of the components with long fluorescence lifetime (480 nm).

The measurement duration of the fluorescence lifetime determination was 1.0 ms or 10 s. The decay curves thus obtained were evaluated using the FluoFit software from Picoquant. The maximum of the measurement curve was determined for Tectosil for this purpose, and the thereof was considered in respect of two abscissa sections. The first is that between the curve maximum ($t_{max}$) and the corresponding timepoint 0.5 ns after the detected maximum intensity ($t_{0.5ns}$) resulting in the fluorescence lifetime $\tau_1$. The second abscissa section encompasses, beginning at an abscissa section 2 ns behind the maximum ($t_{2ns}$), a range of 40 ns (up to $t_{42ns}$), which gives the fluorescence lifetime $\tau_2$. The fluorescence lifetimes are obtained by exponential fitting (exponential tail fit) of the respective curve sections in accordance with the formula $I_{rel}=A*e^{-t/\tau}$. In the case of the residual silicones, the deconvoluted data were evaluated bi-exponentially for the purpose of better reproducibility. This allows a greater reliability of sorting to be ensured.

In general, the recognition of polymers by way of the fluorescence decay constant can be used for the sorting of the materials for the recycling of, for example, thermoplastics, in which case re-use can take place simply. It can also be applied advantageously, furthermore, to plastics which are to be processed chemically, as in the case of the utilization of used thermosets, for example, since in that case the operations can be supplied with a uniform starting material, with which these operations can then be operated more stably. Here it is also possible specifically to recover substances of value, such as platinum catalysts, for example, if they are used in certain operations, since the products thereof are then recognized. Lastly, the method can also be used outside of recycling in order to achieve optical recognition of plastics, as in the case of product control, for example, especially in the case of high-value end products where a variety of starting materials are brought together.

For determining the fluorescence decay times it is not necessary to capture the entire exponential profile; sufficient instead are two or three point or else integral intensity measurements (cumulation—summation—of the individual measurements in each case over a defined time) at different times. In the case of the bi-exponential profile, three intensity measurements are needed. In principle, further measurements are also possible. This allows the accuracy to be improved further.

Integration over a defined timespan in each case—conveniently, the measurements are made before the first half-life, and measurements are made after the first half-life—is of particular advantage here since it considerably improves the signal-to-noise ratio (the fluorescence light of the sample is utilized more efficiently). Assuming customary fluorescence decay times of around 5 ns, the measurements can be made at intervals of one to two nanoseconds, with integration times likewise of around one to two nanoseconds. Measurements with a time resolution of this kind pose no problem electronically. The measuring operation can be simplified further if the plastics sample is excited optically not just once, but instead periodically. It can be assumed that after around ten half-lives, the optical excitation has decayed to an extent such that renewed excitation can take place without disruption; assuming an unfavorable case with a fluorescence decay time of 10 ns, this is achieved after around 70 ns. The plastics sample can therefore be optically excited periodically with a pulse sequence of 70 ns, in other words with a repeat frequency of around 15 MHz. The two measurements for the determination of the fluorescence decay times can be performed with a time shift, with consecutive pulses in particular, and the requirements asked of the electronic components for the evaluation are reduced still further as a result.

Measurement may advantageously take place within a fluorescence decay operation by performing time-shifted detection of the necessary integrated signals under periodic excitation, this measurement being triggered by the excitation pulse; in this case, separation may take place, for example, with a plurality of phase-sensitive detectors (PSD) operating in parallel, via which the intensities are measured, with integration over different time regions of the decay curve. In this case it is not necessary to determine the absolute decay time: here, it is also possible to use instrument-specific raw data, provided they are sufficiently reproducible; with all of the instruments used here, excellent reproducibility of the measurement values has been found, even in the form of raw data (e.g., not corrected by deconvolution). As a result of the unproblematic use even of raw data, the method is simplified considerably further still.

On the assumption that a flake of recyclate has a maximum size, in adverse cases, of 10 mm, and a space between two flakes of 20 mm is left for safety, then more than 1000 excitation pulses per flake would be available, with a pulse sequence of 15 MHz and a rate of advance of 140 m/s (for technological reasons, operation should remain well below the speed of sound).

If these pulses are averaged, the signal-to-noise ratio can be improved considerably and hence the reliability of detection can be increased still further. In the case of a mass of 25 mg for a recyclate flake (the value was obtained by averaging flakes from commercial technical recycling material), half a ton of material per hour can then easily be sorted with a sorting line, for example. In many cases, a sorting output of such a high level is not necessary; in the case of lower sorting output levels, the requirements asked of electronic and mechanical systems are considerably lower.

Using the fluorescence decay time of the intrinsic fluorescence, evaluated mono- and/bi-, tri- or more highly exponentially, it is possible for plastics and their charges to be identified unambiguously and in this way machine-sorted into pure grades for recycling purposes. This relates to all macromolecular compounds, which can therefore be supplied for re-use. The high rate of the recognition process opens up possibilities for sorting units with high throughput of material. Through the use of phase-sensitive detectors and integral measurements, the electronic complexity for detection units can be favorably fashioned. Lastly, the method can be employed for the recognition of macromolecular compounds not only for recycling, but also for applications, such as for product control, for example.

Using the fluorescence decay time of the intrinsic fluorescence, evaluated mono- and bi-, tri- and/or more highly exponentially, it is possible for PET materials, in respect of contamination as a result of their prior use, to be identified unambiguously and in this way machine-sorted into pure grades; this is important particularly for distinguishing between PET material contaminated with mineral oil products, and uncontaminated material, for use in the area of the food-and-drink industry, among others.

Using the fluorescence decay time of the intrinsic fluorescence, evaluated, in particular, bi-, tri- and/or more highly exponentially, it is possible to assign and distinguish silicone materials, as shown here with silicone elastomers and Dehesive films. A more refined evaluation allows conclusions to be made about the processing of the silicone in question. The different catalysts for the production of silicone Dehesive material are reflected, in particular, in the $\tau 2$ time constant, and can be detected efficiently and recovered in pure grades via the auxiliaries such as platinum catalysts. Lastly, the method can also be employed for routine product control, since it is readily automatable.

Using the fluorescence decay time of the intrinsic fluorescence, evaluated mono- and bi-, tri- and/or more highly exponentially, it is also possible, for example, for the PE materials LDPE, HDPE, and UHDPE to be identified unambiguously and to be sorted into pure grades in this way.

In summary, with the aid of the fluorescence decay time constant, plastics and/or their additives can be distinguished simply and with the utmost reliability. The measurement of the fluorescence lifetime—in the case not only of mono-exponential evaluation but also in the case of bi-, tri- or even more highly exponential evaluation—is possible in a simple way with high reliability at the same time. A further advantage is that the measurement of the fluorescence lifetime can be implemented easily and so can be employed in particular in the recycling of large quantities of plastics: the measurement of the fluorescence lifetime and the evaluation thereof takes only a few nanoseconds, and so, for example, plastics flakes are irradiated with the light reliably, on a conveyor belt, for example, and the re-emitted light can then be used for the measurement of the fluorescence lifetime.

With regard to further advantageous embodiments of the apparatus of the invention, reference is made, in order to avoid repetition, to the general part of the description and also to the appended claims.

Lastly, it may expressly be noted that the above-described working examples of the apparatus of the invention serve merely for the discussion of the claimed teaching, without restricting the latter to the working examples.

The invention claimed is:

1. A method for identifying plastics, comprising:
   irradiating at least one sample of a fluorescent marker-free plastic with light of at least one wavelength, wherein irradiating the fluorescent marker-free plastic includes irradiating one or more polymers of the fluorescent marker-free plastic and one or more additives of the fluorescent marker-free plastic, and
   detecting and analyzing light re-emitted by the sample, wherein the light re-emitted by the sample includes light re-emitted by the one or more polymers and by the one or more additives, wherein the fluorescent marker-free plastic is identified from a result of the analysis, characterized in that a fluorescence decay time constant of an intrinsic fluorescence of the fluorescent marker-free plastic is determined from the light detected, wherein the fluorescence decay time constant of the intrinsic fluorescence of the fluorescent marker-free plastic is a combined fluorescence decay time constant of the one or more polymers and the one or more additives, and the one or more polymers and the one or more additives of the fluorescent marker-free plastic are identified from the combined fluorescence decay time constant determined.

2. The method of claim 1, wherein the fluorescence decay time constants are determined and are analyzed multiexponentially.

3. The method of claim 1, wherein the light of at least one wavelength is provided by means of at least one light pulse.

4. The method of claim 3, wherein the light pulses are generated by means of a semiconductor light source.

5. The method of claim 1, wherein the light is generated by means of a laser.

6. The method of claim 1, wherein the re-emitted light is detected by means of one or more phase-sensitive detectors for the subsequent analysis.

7. The method of claim 1, wherein a measured signal of the detected light is integrated over at least one defined timespan for determining the fluorescence decay time constant.

8. The method of claim 7, wherein the measured signal is integrated over a plurality of timespans.

9. The method of claim 8, wherein the measured signal is integrated separately over at least two nonoverlapping timespans, the integrated signals being brought into relation with one another and the fluorescent marker-free plastic, including the one or more polymers and/or the one or more additives, being identified from this relation.

10. The method of claim 7, wherein the at least one timespan corresponds to a falling edge of the measured signal.

11. The method of claim 7, wherein the position of the at least one timespan is chosen before and/or after a customary half-life of a fluorescence lifetime.

12. The method of claim 7, wherein the at least one timespan is between 1 ms and 15 s, between 7.5 s and 12.5 s, or 10 s.

13. The method of claim 3, wherein the fluorescence decay time constant of the fluorescent marker-free plastic to be detected is known approximately, and a selected duration of the at least one light pulse is less than the known fluorescence decay time constant.

14. The method of claim 13, wherein the duration of the at least one light pulse is less than 1 ms, less than 100 ns, less than 10 ns, or between 5 ns and 10 ns.

15. The method of claim 1, wherein the at least one wavelength selected is in the range between 200 nm and 600 nm, between 250 nm and 300 nm, between 375 nm and 450 nm, between 520 nm and 540 nm, between 260 nm and 270 nm, between 400 nm and 410 nm, or between 530 nm and 535 nm.

16. The method of claim 1, wherein when the fluorescent marker-free plastic, including the one or more polymers and/or the one or more additives, has been identified, the identified fluorescent marker-free plastics are separated for recycling by means of a sorting device.

17. The method of claim 1, wherein an optical grating is disposed in a detection beam path of the re-emitted light, and in that the fluorescence decay time constant is determined by means of the zero-order light of the light diffracted by the optical grating.

18. The method of claim 1, wherein the sample is irradiated multiply in succession with light of the at least one wavelength, and the corresponding re-emitted light is measured and analyzed multiply for determining the fluorescence decay time constant.

19. The method of claim 9, wherein the at least two timespans are assigned to temporally different irradiations of the sample with light.

20. The method of claim 1, wherein the detection of the re-emitted light is triggered by the irradiation of the sample with light.

21. An apparatus for implementing the method of claim 1, comprising:
   a light source for irradiating at least one sample of the fluorescent marker-free plastic, including the one or more polymers and/or the one or more additives, with light of at least one wavelength,
   a detector for detecting at least part of the light re-emitted by the sample,
   an analytical unit comprising at least one processor for analyzing the detected light, and
   an identification unit for identifying the fluorescent marker-free plastic, including the one or more polymers and/or the one or more additives, from the result of the analysis provided by the analytical unit, characterized in that the analytical unit is designed to determine a fluorescence decay time constant of the intrinsic fluorescence of the sample from the light detected, and the identification unit is designed to identify the fluorescent marker-free plastic, including the one or more polymers and/or the one or more additives, from the fluorescence decay time constant determined for the sample.

22. The apparatus of claim 21, wherein the light source is a pulsed light source.

23. The apparatus of claim 21, wherein the detector is of phase-sensitive design.

24. The apparatus of claim 21, wherein an optical grating is disposed in a detection beam path of the re-emitted light, the detector being disposed in such a way that the zero order of the light diffracted by the optical grating is detectable by means of the detector, with which the higher orders of the light diffracted by the optical grating is detectable for spectroscopic evaluation.

25. The apparatus of claim 21, wherein a sorting device is disposed which is designed to separate identified plastics from other plastics.

26. The method of claim 1 wherein the fluorescent marker-free plastic is a fluorescent dye-free plastic.

* * * * *